(12) United States Patent
Keggenhoff et al.

(10) Patent No.: US 7,122,701 B2
(45) Date of Patent: Oct. 17, 2006

(54) PROCESS FOR PREPARING AROMATIC AMINES

(75) Inventors: Berthold Keggenhoff, Krefeld (DE);
Karl R. Sittkus, Leverkusen (DE);
Claudia Mueller, Cologne (DE);
Demetrios N. Zervoudis, Monroeville, PA (US)

(73) Assignees: Bayer Aktiengesellschaft, Leverkusen (DE); Bayer Materialscience LLC, Pittsburgh, PA (US)

( * ) Notice: Subject to any disclaimer, the term of this patent is extended or adjusted under 35 U.S.C. 154(b) by 701 days.

(21) Appl. No.: 10/454,332

(22) Filed: Jun. 4, 2003

(65) Prior Publication Data

US 2004/0249213 A1 Dec. 9, 2004

(51) Int. Cl.
*C07C 209/00* (2006.01)

(52) U.S. Cl. ...................................... 564/420
(58) Field of Classification Search ................. 564/209
See application file for complete search history.

(56) References Cited

U.S. PATENT DOCUMENTS

| | | | |
|---|---|---|---|
| 4,720,326 A | 1/1988 | Beckhaus et al. | 203/14 |
| 4,740,621 A * | 4/1988 | Adams et al. | 564/419 |
| 5,345,012 A | 9/1994 | Schieb et al. | 568/934 |
| 6,506,948 B1 | 1/2003 | Sawicki | 568/934 |

FOREIGN PATENT DOCUMENTS

| | | |
|---|---|---|
| GB | 596287 | 1/1948 |
| GB | 2 231 581 | 11/1990 |

* cited by examiner

*Primary Examiner*—Samuel Barts
(74) *Attorney, Agent, or Firm*—Joseph C. Gil; Lyndanne M. Whalen

(57) ABSTRACT

Aromatic amines are produced from aromatic hydrocarbons by
a) reacting the aromatic hydrocarbon(s) with a mixture of nitric acid and sulfuric acid to generate a two-phase reaction mixture,
b) separating the reaction mixture into an aqueous acid phase and an organic phase containing the nitroaromatic compounds
c) washing the organic phase to purify the nitroaromatic compound(s),
d) hydrogenating the nitroaromatic compound(s) in the presence of a catalyst to produce the aromatic amine(s) and water of reaction, and
e) separating the water of reaction formed in step d) from the aromatic amine(s), in which the water of reaction separated in step e) is used to wash the organic phase containing the nitroaromatic compounds in step c).

6 Claims, No Drawings

PROCESS FOR PREPARING AROMATIC AMINES

BACKGROUND OF THE INVENTION

The present invention relates to a process for preparing aromatic amines from aromatic hydrocarbons in which the water of reaction generated during hydrogenation of the nitroaromatic compounds is used to wash the nitrated aromatic compounds obtained by nitrating the corresponding aromatic hydrocarbons.

Aromatic monoamines and diamines, which are used in large amounts as chemical intermediates, for example to produce dyes or plastics, are prepared on an industrial scale by nitrating aromatic hydrocarbons to form nitroaromatic compounds and then hydrogenating the nitroaromatic compounds. In this case, one mole of water per mole of nitro group produced is generated during nitration with nitric acid and two moles of water per mole of amine group are generated during hydrogenation. This water ultimately leaves the process as waste water. Other waste water streams are also produced, particularly during working up of the nitroaromatic compounds which is conventionally performed by separating the acid phase and then washing the nitroaromatic compounds with water and alkaline solutions, generally stepwise and sometimes alternately. This waste water has to be purified in a suitable manner in order to be able to discharge it into the receiving waters in accordance with the pertinent regulations. Thus, for example, U.S. Pat. No. 6,506,948 describes a purification process for waste water which is produced during the preparation of dinitrotoluene.

EP-A-236 839 describes a distillation process for working up aqueous amine solutions such as those generated during the hydrogenation of nitroaromatic compounds. According to EP-A-236 839, the water being produced during distillation can be re-used in chemical processes. However, the concentration of organic impurities (in particular amines) in this water being produced during distillation is in the range from 10–500 ppm. Therefore, the use of this water in chemical processes frequently presents problems because these impurities can lead to difficulties in the processes in which they are present in the re-used water. For example, such re-used water may result in unwanted secondary reactions.

Diaminotoluene, in particular, reacts with dinitrotoluene to give unwanted secondary products, which is expressed, inter alia, in decreasing thermal stability of the dinitrotoluene.

SUMMARY OF THE INVENTION

The object of the present invention is, therefore, to decrease the amount of waste water produced during the preparation of aromatic amines and to increase the economic viability of the aromatic amine preparation process.

Surprisingly, it has been found that water with a considerable concentration of aromatic amine(s) of up to 1000 ppm or more, can be used without any problem to wash the corresponding crude nitroaromatic compound(s) without impairing either the nitration process or the subsequent hydrogenation reaction to produce the aromatic amine(s).

DETAILED DESCRIPTION OF THE INVENTION

The present invention relates to a process for preparing aromatic amine(s) from aromatic hydrocarbon(s), in which
a) aromatic hydrocarbon(s) is/are reacted with a mixture of nitric acid and sulfuric acid to produce a two-phase reaction mixture composed of an aqueous acid phase and an organic phase containing nitroaromatic compound(s),
b) the aqueous acid phase is separated from the two-phase reaction mixture,
c) the organic phase containing the nitroaromatic compound(s) is/are purified by washing the organic phase and removing the wash water or solution, and, optionally, isolating the nitroaromatic compound(s),
d) the nitroaromatic compound(s) is/are hydrogenated in the presence of a catalyst to produce the corresponding aromatic amine(s) with the formation of water of reaction, and
e) the water of reaction formed in step e) is separated from the aromatic amine(s).

An important feature of the present invention is the use of the water of reaction separated in step e) to wash the organic phase containing the nitroaromatic compound(s) in step c).

Any of the industrially significant aromatic amines may be produced in accordance with the process of the present invention. Aniline and ring-substituted anilines such as toluidine and chloraniline are examples of monoamines and diaminotoluene is an example of a diamine that may be produced by the process of the present invention. The process of the present invention is particularly suitable for preparing diaminotoluene (2,4- and 2,6-diaminotoluene).

In step a), any aromatic hydrocarbon, preferably benzene or toluene, is nitrated with a mixture of nitric acid and sulfuric acid in known manner. The two-phase reaction mixture obtained is separated in step b) into an organic and an acid phase. Phase separation can be performed in static separators or in centrifuges. The organic phase is composed substantially of the crude nitroaromatic compound(s) which is/are purified, preferably, by multi-stage washing prior to hydrogenation.

In the present invention, the water of reaction recovered from the hydrogenated mixture in the later step e) is used as wash water in step c). Conventionally, the organic phase is washed several times. In the first wash, water is used to remove residual sulfuric acid. From 1 to 100 parts by wt. of water, preferably 5 to 50 parts by wt. of water per 100 parts by wt. of organic phase are used to wash the organic phase. For this purpose, the water of reaction generated during hydrogenation of the nitroaromatic compound(s) and separated in step e), can be used directly as wash water. However, the wash water from a subsequent step in the process, preferably, wash water separated in the last wash step, can also be used as wash water in the first wash step. However, especially when the organic phase has a low concentration of acid, this first wash step with water may be omitted.

After the organic phase has been washed with water or directly after separation from the aqueous acid phase (if the acid concentration in the organic phase is sufficiently low that the first water wash may be omitted), the organic phase is normally washed with an alkaline wash liquid, such as dilute caustic soda or soda solution, to remove weakly acid secondary products, such as phenols or organic acids. In this case, 0.1 to 2 parts by wt. of caustic soda solution (100%) or soda per 100 parts by wt. of organic phase in the form of a 0.5 to 20% strength, or a fully saturated, solution are normally used. In accordance with the present invention, the water of reaction recovered in step e) may also be used as the dissolution or dilution water for the alkaline wash liquid.

After the alkaline wash step, a third and additional, optional, wash steps may be performed using water. In the third and any other additional wash step(s), from 1 to 100 parts by wt. of water, preferably from 5 to 50 parts by wt. of water, are used for each 100 parts by wt. of organic phase. The water of reaction recovered in step e) can be used for the third and, optionally, any further wash steps. All or some of the water used for washing in this/these wash steps, which is separated, can then be used as wash water in the first wash step for the organic phase generated in a subsequent nitration reaction.

The water of reaction generated during hydrogenation of the nitroaromatic compounds, and separated in step e), is preferably used as wash water for the third and/or any optional further washings of the organic phase and the water resulting from these wash steps is preferably used as wash water in the first wash step for the organic phase generated in a subsequent nitration reaction.

When preparing aniline, a total of about 29 parts by wt. of water of reaction from step e) per 100 parts by wt. of nitrobenzene are generally available as wash water. When preparing diaminotoluene, about 40 parts by wt. of water of reaction from step e) per 100 parts by wt. of dinitrotoluene are generally available as wash water. This available wash water can be used, for example, entirely in the third and/or optionally further wash steps or distributed over all the wash steps. If the amount of wash water required is larger than the available water of reaction from step e), then pure water can additionally be used.

All of the wash steps can be performed in industrially conventional mixer/separator equipment or in wash and extraction columns, in a single step or in several steps. When one wash step is carried out in several stages, the wash liquid is preferably passed in countercurrent.

Each of the aqueous phases being produced in the wash steps is, as a rule, supplied as a waste water stream to the waste water working-up unit, if it is not used as wash water for subsequent wash steps. After passing through all the wash steps, the organic phase obtained is the technical grade pure nitroaromatic compound.

In step d), the nitroaromatic compound is reacted with hydrogen in the presence of a catalyst to form the aromatic amine. Depending on the boiling point and stability of the starting component, this hydrogenation may be performed in the gas phase or in the liquid phase, with or without the use of an auxiliary solvent. The reaction conditions, the design of the apparatus and the choice of catalyst are known from the prior art. (See, e.g. U.S. Pat. No. 6,080,890 for aniline or DE-A-44 35 839 for diaminotoluene.) The reaction mixture obtained, after reaction and, optionally, after separation of the catalyst, is an amine/water mixture which may be present as a single phase or as two phases, depending on the amine.

In step e), the water of reaction is separated from the amine/water mixture. If the amine/water mixture is present in two phases (as is the case, for example, when preparing aniline), then the mixture is normally first separated into a water-rich phase and an amine-rich phase. Phase separation, in this case, is typically performed in separating vessels. Normally, the dissolved water, together with some of the amine, is then distilled out of the organic phase and the distillate is returned to the separating vessel. Organic components (substantially amine) are removed from the aqueous phase in a stripping column down to the point where the concentration of organic components is preferably less than 0.1 wt. %, most preferably less than 100 ppm. The amount of water obtained is, for example, in the case of aniline, about 39 parts by wt. per 100 parts by wt. of amine. The water purified in this way is then used, in accordance with the invention, in step c) for washing the nitroaromatic compound.

If the amine/water mixture is present as a single phase (as is the case during the preparation of diaminotoluene), then the mixture, after separation of any optionally present auxiliary solvent, is separated by distillation into the high-boiling amine (as the product remaining at the base of the column), volatile secondary products and water (as the middle fraction). A process similar to the one described, for example, in EP-A-236 839 may be used. Here again, a water phase with a concentration of organic components (substantially amine) of preferably less than 0.1 wt. %, most preferably less than 100 ppm, is produced. The amount of water obtained is, for example, in the case of diaminotoluene, about 59 parts by wt. per 100 parts by wt. of amine. The water purified in this way is then used, in accordance with the invention, in step c) for washing the nitroaromatic compounds.

Having thus described our invention, the following Examples are given as being illustrative thereof.

EXAMPLES

Example 1

Separating the Water of Reaction from the Reaction Solution from Hydrogenation

A bubble-cap column with a 50 mm diameter having 30 plates and a lateral withdrawal facility at the 20th plate was used. This column was operated at an absolute pressure of 3 bar and a base temperature of about 200° C. A reaction mixture of about 60 wt. % toluene diamine (TDA) isomer mixture with a concentration of organic secondary products of 0.5 wt. % and a water content of about 40 wt. % was obtained from the catalytic hydrogenation of dinitrotoluene (DNT) with hydrogen. This reaction mixture was introduced at the 5th plate in the column at a rate of 2 kg/h. By supplying heat at the base of the column, 1100 g/h of vapors were produced at the head of the column. These vapors were condensed and returned to the column as a reflux stream and 15 g/h of distillate, which contained the volatile secondary products, were discharged. 1250 g of TDA isomer mixture with a 4 wt. % content of water were continuously removed as the base product. Furthermore, 735 g/h of water were removed at the lateral discharge point at the 20th plate. This water had a residual concentration of organic amines of 300 ppm (0.03 wt. %) and was used to wash crude DNT.

Example 2

Washing Crude DNT with the Water of Reaction from Hydrogenation

Three mixer/separators in series, each composed of a 1 liter stirred flask and a 1 liter separating vessel, were used in this Example. 1900 g/h of crude DNT with a concentration of 1.2 wt. % of sulfuric acid, 0.8 wt. % of nitric acid and 0.6 wt. % of cresols and organic acids, a mixture like the one obtained from the two-step reaction of toluene with nitrating acid, was placed in this mixer/separator battery at 70° C. The washed DNT from each stage was supplied as the lower phase in the next stirred vessel in the series from each separating vessel in a siphon action. Technical grade pure DNT was obtained from the last separating vessel.

In the first stirred vessel, 200 g/h of the water of reaction obtained in Example 1 were added as wash liquid. In the second stirred vessel, 200 g/h of 5 wt. % strength soda solution were added. In the third vessel, 535 g/h, that is, the remainder of the available stream of the water of reaction obtained in Example 1 was added. The aqueous upper phase from all three separating vessels was allowed to run off as waste water.

The washed DNT obtained in this way complied with all the purity requirements for technical grade products, i.e, a neutral pH and a concentration of organic acids and cresols of less than 200 ppm.

Although the invention has been described in detail in the foregoing application for the purpose of illustration, it is to be understood that such detail is solely for that purpose and that variations can be made therein by those skilled in the art without departing from the spirit and scope of the invention, except as it may be limited by the claims.

What is claimed is:

1. A process for the production of an aromatic amine comprising:
    a) reacting an aromatic hydrocarbon with a mixture of nitric acid and sulfuric acid to form a two-phase reaction mixture,
    b) separating the two-phase reaction mixture into an aqueous acid phase and an organic phase containing nitroaromatic compound,
    c) washing the organic phase to purify the nitroaromatic compound,
    d) hydrogenating the nitroaromatic compound in the presence of a catalyst to produce an aromatic amine and water, and
    e) separating the water produced in step d) from the aromatic amine, in which the water separated in step e) is used to wash the organic phase containing the nitroaromatic compounds in step c).

2. The process of claim 1 in which the water separated in step e) has a concentration of organic compounds of less than 0.1 wt. %.

3. The process of claim 1 in which the water of reaction separated step e) has a concentration of organic compounds of less than 100 ppm.

4. The process of claim 1 in which step c) is performed in two or more stages.

5. The process of claim 4 in which all or some of the water of reaction separated step d) is used in the last wash stage.

6. The process of claim 5 in which the wash water resulting from the last stage is used as wash water in the first wash stage.

* * * * *